(12) United States Patent
Shiota et al.

(10) Patent No.: US 8,951,397 B2
(45) Date of Patent: Feb. 10, 2015

(54) ELECTROPHORETIC ANALYSIS METHOD

(75) Inventors: Kazuma Shiota, Matsudo (JP);
Tomohiro Fujita, Matsudo (JP)

(73) Assignee: Godo Shusei Co., Ltd., Tokyo (JP)

( * ) Notice: Subject to any disclaimer, the term of this patent is extended or adjusted under 35 U.S.C. 154(b) by 364 days.

(21) Appl. No.: 13/503,040

(22) PCT Filed: Nov. 17, 2010

(86) PCT No.: PCT/JP2010/070431
§ 371 (c)(1),
(2), (4) Date: Apr. 20, 2012

(87) PCT Pub. No.: WO2011/062174
PCT Pub. Date: May 26, 2011

(65) Prior Publication Data
US 2012/0199480 A1    Aug. 9, 2012

(30) Foreign Application Priority Data

Nov. 18, 2009 (JP) .................................. 2009-262496

(51) Int. Cl.
*G01N 33/50* (2006.01)
*C12N 9/52* (2006.01)
*C07K 1/26* (2006.01)
*G01N 27/447* (2006.01)

(52) U.S. Cl.
CPC ... *C12N 9/52* (2013.01); *C07K 1/26* (2013.01); *G01N 27/447* (2013.01)
USPC ...................................................... 204/456

(58) Field of Classification Search
CPC .................. G01N 27/44747; G01N 27/44704; G01N 27/447; G01N 27/4473; G01N 27/44739; B01L 2400/0415; B01L 2400/0421; B01L 2400/0418; B01D 57/02; C12Q 2565/125; C07K 1/26; G02F 1/167; C12N 15/101
USPC ................................................. 204/450–470
See application file for complete search history.

(56) References Cited

U.S. PATENT DOCUMENTS 3,930,954 A    1/1976 Irie
3,948,725 A    4/1976 Irie

FOREIGN PATENT DOCUMENTS

| CN | 101487002 A | 7/2009 |
|---|---|---|
| JP | 56-78589 | 6/1981 |

(Continued)

OTHER PUBLICATIONS

P. Secades and J. A. Guijarro, "Purification and characterization of an extracellular protease from the fish pathogen *Yersinia ruckeeri* and effect of culture conditions on production" Applied and Environmental Microbiology, vol. 65, No. 9, Sep. 1999, p. 3969-3975.*

(Continued)

*Primary Examiner* — J. Christopher Ball
(74) *Attorney, Agent, or Firm* — Oblon, Spivak, McClelland, Maier & Neustadt, L.L.P.

(57) ABSTRACT

Provided is a means for accurately analyzing a protease by electrophoresis.
Disclosed is an electrophoretic analysis method for analyzing a protease-containing sample, is characterized by exposing a sample containing a protease to be analyzed, to pH conditions under which the protease is rapidly deactivated, and then subjecting the sample to electrophoresis.

20 Claims, 18 Drawing Sheets

(56) References Cited

FOREIGN PATENT DOCUMENTS

| JP | 56 51747 | 12/1981 |
| JP | 57 14836 | 3/1982 |

OTHER PUBLICATIONS

Chinese Office Action issued Aug. 20, 2013, in China Patent Application No. 201080051899.X.
Weh-hua Huang, et al., "Analysis of protease in koji of soy sauce by modified SDS-Page method", China Brewing, No. 3, serial No. 156, Analysis and Examination, 2006, pp. 60-62 (with English Abstract).
Shibata, M. et al., "A Novel Metalloproteinase, Almelysin, from a Marine Bacterium, *Alteromonas* sp. No. 3696: Purification and Characterization," Bioscience, Biotechnology and Biochemistry, vol. 61, No. 4, pp. 710-715, (1997).
Sugiyama, S., et al., "Purification and Characterization of Six Kiwifruit Proteases Isolated with Two Ion-exchange Resins, Toyopearl-SuperQ and Bakerbond WP-PEI," Bioscience, Biotechnology and Biochemistry, vol. 60, No. 12, pp. 1994-2000, (1996).
Kameyama, K., et al., "Sample preparation method for poorly soluble proteins prior to two-dimensional electrophoresis," Seibutsu Butsuri Kagaku, vol. 48, No. 2, pp. 71-73, (2004) (with English abstract).
Tezel, T.P., et al., "Posterior Vitreous Detachment With Dispase," Retina, vol. 18, No. 1, pp. 7-15, (1998).
Laemmli, U.K., "Cleavage of Structural Proteins during the Assembly of the Head of Bacteriophage T4," Nature, vol. 227, pp. 680-685, (1970).
International Search Report Issued Jan. 25, 2011 in PCT/JP10/70431 Filed Nov. 17, 2010.
Extended European Search Report issued Apr. 2, 2013 in Patent Application No. 10831568.0.
Kurt S. Stenn, et al., "Dispase, a Neutral Protease From *Bacillus polymyxa*, is a Powerful Fibronectinase and Type IV Collagenase", Journal of Investigative Dermatology, Nature Publishing Group, GB, ISSN: 0022-202X, DOI: 10.1111/1523-1747.EP12277593A, XP001070905, vol. 93, No. 2, Aug. 1, 1991, pp. 287-290.
Hittu Matta, et al., "Isolation and partial characterization of a thermostable extracellular protease of *Bacillus polymyxa* B-17", International Journal of Food Microbiology, Elsevier Science Publishers, Amsterdam, NL, ISSN: 0168-1605, XP002687438A, vol. 42, No. 3, Jul. 21, 1998, pp. 139-145.
Junko Sakai, et al., "Proteolytic enzymes of squid mantle muscle", Comparative Biochemistry and Physiology Part B: Comparative Biochemistry, Pergamon Press, London, GB, ISSN: 0305-0491, DOI: 10.1016/0305-0491 (81) 90145-0 [retrieved on Jan. 1, 1981], XP025709338A, vol. 68, No. 3, Jan. 1, 1981, pp. 389-395.
Manuel Diaz-López, et al., "Characterization of fish acid proteases by substrate-gel electrophoresis", Comparative Biochemistry and Physiology Part B, Biochemistry & Molecular Biology, Elsevier, Oxford, GB, ISSN: 1096-4959, DOI: 10.1016/S0305-0491 (98) 10123-2 [retrieved on Dec. 1, 1998], XP027066610A, vol. 121, No. 4, Dec. 1, 1998, pp. 369-377.
Benjamin O. Fagbemi, et al., "Partial purification and characterisation of the proteolytic enzymes of *Fasciola gigantica* adult worms", Veterinary Parasitology, Elsevier Science, Amsterdam, NL, ISSN: 0304-4017, DOI: 10.1016/0304-4017(91)90102-2 [retrieved on Nov. 1, 1991], XP023986582A, vol. 40, No. 3-4, Nov. 1, 1991, pp. 217-226.
K. H. S. Swamy, et al., "Isolation and Characterization of Protease Do from *Escherichia coli*, a Large Serine Protease Containing Multiple Subunits", Archives of Biochemistry and Biophysics, Academic Press, US, ISSN: 0003-9861, DOI: 10.1016/0003-9861(83)90242-4 [retrieved on Jul. 15, 1983], XP024809549, vol. 224, No. 2, Jul. 15, 1983, pp. 543-554.
Communication pursuant to Article 94(3) EPC issued Jul. 28, 2014 in European Patent Application No. 10 831 568.0.
Greg R. Germaine, et al., "Proteolytic activity of *Candida albicans*: action on human salivary proteins", Infection and Immunity, vol. 22, No. 3, XP55130191, Dec. 1978, pp. 861-866 with cover page.

\* cited by examiner

ELECTROPHORETIC ANALYSIS METHOD

FIELD OF THE INVENTION

The present invention relates to an electrophoretic analysis method capable of accurately measuring the purity of a protease.

BACKGROUND OF THE INVENTION

In the fields that handle animal cells, a wide variety of enzymatic treatments of cultured cells are being carried out. Particularly, since the extracellular matrix and the like that constitute the basement membrane can be degraded under mild conditions by using enzymes, enzymatic treatments are indispensable in the subculture of cultured cells. As the enzymes to be used herein, proteases such as trypsin and collagenases, or glycolytic enzymes such as hyaluronidases are well known.

Bacillolysin is a neutral metalloprotease produced by microorganisms, particularly the bacteria of the genus *Bacillus* and related genera. A protease which is one kind of bacillolysin was found from a culture of microorganism *Bacillus polymyxa* (the genus name has been changed to genus *Paenibacillus* since 1994). This protease was acknowledged to have a degrading action that is different from that of trypsin or collagenases, and for example, the protease can disperse cell clusters that cannot be thoroughly dispersed by other enzymes, into single cells without damaging the cells themselves. Furthermore, this protease is used in various fields, such as the use in the culturing of adhesive cells in a suspension system by utilizing the nature that the protease is not inhibited in the blood serum (Patent Documents 1 and 2). This protease is sold under the name "Dispase (registered trademark)" from Godo Shusei Co., Ltd., and is widely used over the world.

Currently, in the field related to regenerative medicine, for example, such as in the case of culturing epithelial cells separated from a skin tissue and preparing the cells in a sheet form, or in the case of preparing insulin-producing cells from the pancreas, this protease (Dispase) is most generally used. Furthermore, investigations are being conducted on the utilization of bacillolysin as a pharmaceutical product not only for the laboratory uses and industrial uses as described above, but also for the auxiliary uses for medical purposes, particularly at the time of removing the vitreous body during the surgery for proliferative retinopathy in the ophthalmologic field, or for the use in a prophylactic therapy for diabetic cataract (Non-Patent Document 1).

Enzymes have been utilized as pharmaceutical products for a relatively long time, but at first, the use was limited only to the utilization of proteases, amylases, lipases and the like as digestion accelerators. Many of these are orally administered, so that there has been hardly any case, to date, where purity causes a problem. However, treatment methods based on the non-oral administration of enzymes were commenced, such as a supplement therapy for metabolic disorder diseases or the use of a group of enzymes that participate in the blood coagulation system, and therefore, those enzymes serving as pharmaceutical products are now demanded to have a purity necessary for non-oral administration, or to have impurities eliminated therefrom, such as to have allergy-inducing substances or endotoxins eliminated. At the same time, high purity is also required of enzyme proteins as bulk drug substances, so as to prevent any unexpected adverse side effects in advance.

Conventionally, there are occasions in which a gel filtration method is used as a method for analyzing the purity of a protein; however, the gel filtration method lacks the resolution capability for discriminating a molecular weight difference of several thousands in proteins having molecular weights of several ten thousands. On the other hand, an electrophoresis method has high resolution capability, and is widely used as a method for analyzing the purity of a protein. Particularly, an SDS-polyacrylamide gel electrophoresis method (SDS-PAGE method) in which a sample is heated in advance together with SDS to SDS-fy the sample, and the resulting sample is electrophoresed in the presence of SDS, is considered as an excellent method that can analyze the purity of a purified protein, together with a capillary electrophoresis method of similarly performing electrophoresis in the presence of a surfactant (Non-Patent Document 2).

PRIOR ART DOCUMENTS

Patent Document

Patent Document 1: Japanese Patent Application Publication (JP-B) No. 56-51747
Patent Document 2: JP-B No. 57-14836

Non-patent Document

Non-Patent Document 1: Tezel T H, et al., Retina, 1998; 18 (1)
Non-Patent Document 2: Laemmli et al., Nature, 227, 680-685 (1970)

SUMMARY OF THE INVENTION

Problem to be Solved by the Invention

However, when an electrophoretic analysis accompanied by an SDS treatment was carried out on a neutral metalloprotease such as the protease described above (Dispase), it was found that a large number of bands came to be detected. Furthermore, it was found that the occurrence of this large number of bands could never be prevented by high temperature conditions or by the addition of a commercially available protease inhibitor. Therefore, the purity of this protease in a sample containing the protease could not be measured, and also, it was completely unknown about what degree of purity the purified protease acquired.

An object of the present invention is to provide a means for accurately analyzing various proteases by electrophoresis.

Solution to Problem

Thus, the inventors of the present invention conducted extensive investigations so that the degradation of proteases during an SDS treatment can be prevented. First, protein denaturants such as guanidine and urea were added so that autodegradation of proteases could be prevented, but as expected, degradation was observed. Furthermore, since the protease described above is a metalloprotease, the addition of a metal chelating agent was also investigated. However, the activity was not instantly terminated, but gradual deactivation of the enzyme was observed. Thus, it was found that the enzymes having residual activity were engaged in autodegradation, and as a result, the original purity was not reflected. Thus, the inventors further conducted an investigation. The inventors first thought that if the protease is subjected to a strong acid or a strong base, an accurate analysis cannot be carried out because chemically effective hydrolysis proceeds; nevertheless, completely surprisingly, the inventors found that when the pH is adjusted to a pH at which the protease is rapidly deactivated, and then the protease is subjected to electrophoresis, autodegradation is suppressed, and chemical hydrolysis caused by an acid or a base can also be suppressed, so that the main band of the protease is observed, and an accurate purity measurement can be made possible. Furthermore, for the protease described above (Dispase), its purity could be checked for the first time, and a high purity product having a purity of 92% or higher was obtained for the first time.

That is, the present invention is to provide a method for electrophoretically analyzing a protease-containing sample, the method including exposing a sample containing a protease to be analyzed, to pH conditions under which the protease is rapidly deactivated, and then subjecting the sample to electrophoresis.

Furthermore, the present invention is to provide a protease which: (1) is produced by a bacterium belonging to the genus *Paenibacillus*; (2) degrades casein and hemoglobin in a neutral pH range; (3) has an optimum pH of 7.0 to 8.0, is stable at pH 5.5 to 9.0; (4) works at 20° C. to 75° C., has an optimum temperature of 55° C.; and (5) has a molecular weight estimated to be 32,000 to 34,000 Da according to an electrophoresis method, which protease is identified to have a purity of 92% or higher by the analysis method described above.

Effects of Invention

When electrophoresis was carried out after a treatment under the pH conditions according to the present invention, the original purity of a protease which is susceptible to autodegradation was clearly defined. Particularly, for the specific protease described above, the purity calculation was made possible for the first time by the present invention. This protease that has been purified to a purity of 92% or higher, and particularly to a purity of 95% or higher, is useful for medicinal applications, and can serve as a pharmaceutical product having fewer side effects.

DESCRIPTION OF EMBODIMENTS

Figure 1:
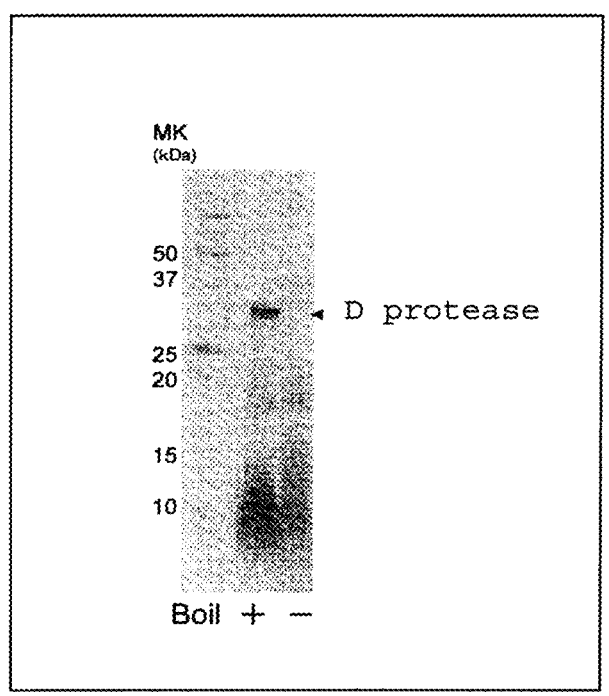
FIG. 1 shows the results of SDS-PAGE of Dispase I according to a conventional method.

The electrophoretic analysis method of the present invention is characterized by exposing a sample containing a protease to be analyzed, to pH conditions under which the protease is rapidly deactivated, and then subjecting the sample to an electrophoretic analysis.

As the protease to be analyzed, there are no particular limitations as long as it is a protease, and any of acidic proteases, neutral proteases and alkaline proteases can be used.

Specific examples of the protease to be analyzed include serine proteases such as chymotrypsin (optimum pH 7.8), trypsin (optimum pH 8.0), subtilisin (optimum pH 7 to 10.5), and protease K (optimum pH 7.5 to 12); cysteine proteases such as papain (optimum pH 6 to 7.5); asparagine proteases such as pepsin (optimum pH 2 to 3); metalloproteases such as thermolysin (optimum pH 7) and BNP (optimum pH 7.0 to 8.0); and the like. Among these, those neutral proteases having their optimum pH at near neutrality are preferred, neutral metalloproteases are more preferred, and the protease described in Patent Document 1 (hereinafter, referred to as D protease) is particularly preferred.

As the sample containing the protease to be analyzed of the present invention, a sample containing a protease with unknown purity obtained in the process of producing the protease from a cell culture of a microorganism or the like by a routine method, a sample containing a purified protease with unknown purity, a sample containing a protease to be analyzed and other proteins, a commercially available protease with unknown purity, and the like can be used. Examples of purification techniques for obtaining a protease from a culture include adsorption, solvent fractionation, ammonium sulfate fractionation, chromatography, crystallization, and the like. Examples of commercially available proteases include the various proteases described above, Dispase I, Dispase II (registered trademark), and the like.

According to the present invention, a sample containing a protease to be analyzed is exposed to pH conditions under which the protease is rapidly deactivated. The pH at which a protease is rapidly deactivated means a pH at which the protease activity disappears within one minute, and particularly, a pH at which the protease activity disappears within 10 seconds is preferable. Usually, such pH conditions are preferably pH conditions that are away from the optimum pH by a value of 3 or greater, and more preferably pH conditions that are away from the optimum pH by a value of 4 or greater.

The more preferred pH conditions under which a protease is rapidly deactivated are such that, when the protease is a neutral protease, pH 0.1 to 3 or pH 11 to 14 is preferred, and pH 0.1 to 2.0 or pH 12 to 14 is more preferred. When the protease is an acidic protease, pH 10 to 14 is preferred, and pH 11 to 14 is more preferred. When the protease is an alkaline protease, pH 0.1 to 4 is preferred, and pH 0.1 to 3 is more preferred.

When the protease is D protease, it is preferable to adjust the pH to 0.7 to 2.0. At a pH value of less than 0.7, chemical hydrolysis of the protease occurs, and at a pH value of higher than 2.0, autodegradation cannot be suppressed. The pH value is more preferably 0.9 to 1.9, and particularly preferably 1.5 to 1.9.

For the adjustment of pH, an acid or an alkali may be added to the protease-containing sample. Examples of such an acid include sulfuric acid, hydrochloric acid, phosphoric acid, nitric acid, trichloroacetic acid, and the like. Examples of such an alkali include sodium hydroxide, potassium hydroxide, calcium hydroxide, lithium hydroxide, sodium carbonate, potassium carbonate, sodium hydrogen carbonate, potassium hydrogen carbonate, and the like.

The time and temperature to be employed under such pH conditions may be any time and temperature at which the subject protease is deactivated and chemical hydrolysis does not occur. For example, it is preferable to set the time and temperature conditions to 1 to 30 minutes at 25° C., and more preferably to 1 to 10 minutes at 25° C.

Since the sample containing a protease to be analyzed has lost its activity due to the pH treatment described above, after the relevant pH treatment, the sample may be directly subjected to electrophoresis, or may be subjected to electrophoresis after the pH of the sample is adjusted to near neutrality or alkalinity. That is, the pH at the time of being supplied to an electrophoresis apparatus is not particularly limited.

Thereafter, the sample containing a protease to be analyzed may be subjected to electrophoresis by a conventional method. Examples of electrophoresis techniques include SDS-PAGE, capillary electrophoresis, native-PAGE, and isoelectric point electrophoresis. For example, in the case of SDS-PAGE, the relevant protease-containing sample may be mixed with an equal amount of a sample treatment liquid containing SDS, mercaptoethanol, and Bromophenol Blue dye, and then the mixture may be subjected to PAGE. Meanwhile, in the case of using a sample containing the D protease described above, boiling is not needed in the SDS treatment stage. On the contrary, if a sample at pH 0.7 to 2.0 is boiled, there is a possibility that the protease may be degraded. Therefore, the SDS treatment is preferably carried out at 10° C. to 30° C.

Furthermore, in the case of capillary electrophoresis, the pH-treated protease-containing sample may be added to a sample treatment liquid shown for each apparatus (Experion Pro260 Analysis Kit, manufactured by Bio-Rad Laboratories, Inc.; or the like), and the liquid mixture may be supplied to a capillary electrophoresis apparatus (Experion, fully automated chip electrophoresis apparatus, manufactured by Bio-Rad Laboratories, Inc.; or the like).

In regard to the analysis technique after the electrophoresis, for example, a dye on gel may be detected, and the like, or the purity may be converted into a value using, for example, a densitometer. Furthermore, the purity can be calculated also by using capillary electrophoresis.

According to the method of the present invention, the purity of various proteases, particularly of D protease, can be accurately measured by an electrophoresis method. Therefore, when the method of the present invention is used, D protease having a purity of 92% or higher, which is conventionally unavailable, can be identified. A D protease which has been confirmed by the method of the present invention to have a purity of 92% or higher, more preferably 95% or higher, even more preferably 98% or higher, and particularly preferably 99% or higher, can be used as a pharmaceutical product in particular.

Here, it is described in Patent Document 1 that D protease has the following properties. It is a protease which: (1) is produced by a bacterium belonging to *Bacillus polymyxa*; (2) degrades casein and hemoglobin in a neutral pH range; (3) has an optimum pH of 8.5, is stable at pH 4.0 to 9.0; (4) works at 20° C. to 75° C., has an optimum temperature of 60° C.; (5) has its activity enhanced by $Ca^{2+}$, $Mn^{2+}$, $Mg^{2+}$, $Fe^{2+}$, $Fe^{3+}$ or $Al^{3+}$; and (6) has a molecular weight of 35900 Da as measured according to an ultracentrifugation method.

However, the inventors of the present invention reinvestigated the properties of D protease this time, and the protease was found to have the following properties. It is speculated that D protease: (1) is produced by a bacterium belonging to the genus *Paenibacillus*; (2) degrades casein and hemoglobin in a neutral pH range; (3) has an optimum pH of 7.0 to 8.0; (4) is stable at pH 5.5 to 9.0; (4) works at 20° C. to 75° C., has an optimum temperature of 55° C.; and (5) has a molecular weight according to an electrophoresis method of 32,000 to 34,000 Da. Meanwhile, the species name of *Bacillus polymyxa* has been changed at present to *Paenibacillus polymyxa*.

In addition, more specifically, D protease has the following properties.

(1) Action

D protease exhibits properties that are generally exhibited by neutral proteases, and degrades proteins such as casein and hemoglobin in a neutral pH range to produce peptides or free amino acids.

In connection with the B chain of oxidized insulin, it has been confirmed that D protease cleaves peptide bonds at 12 sites, namely, Pha(1)-Val(2), His(5)-Leu(6), His(10)-Leu(11), Glu(13)-Ala(14), Ala(14)-Ler(15), Ler(15)-Tyr(16), Tyr(16)-Leu(17), Leu(17)-Val(18), Gly(23)-Phe(24), Phe(24)-Phe(25), Phe(25)-Tyr(26) and Lys(29)-Ala(30).

(2) Substrate Specificity

D protease exhibits a mild proteolytic action against casein.

(3) Optimum pH and Stable pH Range a. Optimum pH: The optimum pH for the proteolytic action against casein is 7.0 to 8.0.

b. Stable pH range: D protease is very stable in the range of pH 5.5 to 9.0.

(4) Range of Working Optimum Temperature

D protease works in the range of 20° C. to 75° C., and the optimum temperature is 55° C.

(5) Conditions for Deactivation by pH, Temperature or the Like

D protease completely loses its activity at pH 3.0 or lower and at pH 10.0 or higher. Further, D protease completely loses its activity by a heating treatment at 65° C. for 10 minutes.

(6) Inhibition, Activation and Stabilization

D protease is inhibited by metal chelating agents such as ethylenediamine tetraacetate (EDTA), citric acid, O-phenanthroline, 2,2-dipyridyl and sodium fluoride, and oxidizing agents such as N-bromosuccinimide (NBS) and iodine.

D protease is stabilized by calcium ion, and activation thereof requires zinc ion.

(7) Molecular Weight

The molecular weight according to an electrophoresis method is speculated to be 32,000 to 34,000 Da.

EXAMPLES

Hereinafter, the present invention will be described in detail by way of Examples.

Reference Example 1

Analysis by SDS-PAGE Accompanied by Conventional Pretreatment Method

Commercially available Dispase I (manufactured by Godo Shusei Co., Ltd.) was dissolved in a 50 mM Tris-2 mM calcium acetate buffer solution (pH 7.5) so that the protein concentration was 1 mg/mL. To 100 µL of this solution, 100 µL of a conventional sample pretreatment liquid (containing 25% glycerin, 2.5% SDS, 0.125 M Tris-hydrochloric acid buffer solution pH 6.8, 2-mercaptoethanol 2.5%, and an appropriate amount of Bromophenol Blue) was added. Two samples were prepared, and one of them was boiled for 3 minutes.

The samples treated such as described above were subjected to SDS-PAGE (15% gel) in an amount of 10 µL each.

As a result, as shown in FIG. 1, a large number of bands were detected for Dispase I in the SDS-PAGE carried out using a conventional pretreatment method. The molecular weight of D protease, which is a main component of Dispase I, was found to be 32 kDa to 34 kDa, but a number of bands indicating smaller molecular weights than the band indicating the relevant molecular weight were detected. Furthermore, in the sample that was not boiled, a band corresponding to D protease was not detected, perhaps because the sample was not SDS-fied.

Reference Example 2

Analysis of Purified Enzyme According to Conventional Pretreatment Method

Commercially available Dispase I (manufactured by Godo Shusei Co., Ltd.) was dissolved in a 50 mM Tris-2 mM calcium acetate buffer solution (pH 8.0) so that the protein concentration was 0.4 mg/mL. 200 mL of this solution was adsorbed to an anion exchange resin TSK GEL DEAE 650M column (3×20 cm) that has been equilibrated in advance with a 50 mM Tris-2 mM calcium acetate buffer solution (pH 8.0), and was eluted at a linear gradient with a 50 mM Tris-2 mM calcium acetate buffer solution (pH 8.0) containing 0.1 M sodium chloride. The chromatography operation was carried out at near 4° C. The eluted fractions of D protease were combined and concentrated by means of an UF membrane (AIP manufactured by Asahi Kasei Corp.). The concentrated D protease was subjected to desalination using a 50 mM Tris-2 mM calcium acetate buffer solution, and crystals were precipitated. These crystals were designated as a purified enzyme.

The purified enzyme was dissolved in a 50 mM Tris-2 mM calcium acetate buffer solution (including 0.2 M sodium chloride, pH 7.5) so that the protein concentration was 1 mg/mL, and the solution was subjected to gel filtration HPLC (G2000SWXL manufactured by Tosoh Corp.). A peak corresponding to D protease was detected at a retention time of 18 to 20 minutes. It was speculated that this peak corresponded to a molecular weight of 30 kDa to 40 kDa, according to a comparison with a separate molecular weight marker.

To the sample dissolved for the use in gel filtration HPLC, 100 µL of a conventional sample pretreatment liquid (containing 25% glycerin, 2.5% SDS, 0.125 M Tris-hydrochloric acid buffer solution pH 6.8, 2-mercaptoethanol 2.5%, and an appropriate amount of Bromophenol Blue) was added, and the resulting mixture was boiled for 3 minutes.

The sample thus treated was subjected to SDS-PAGE (15% gel) in an amount of 10 µL each.

Figure 2:
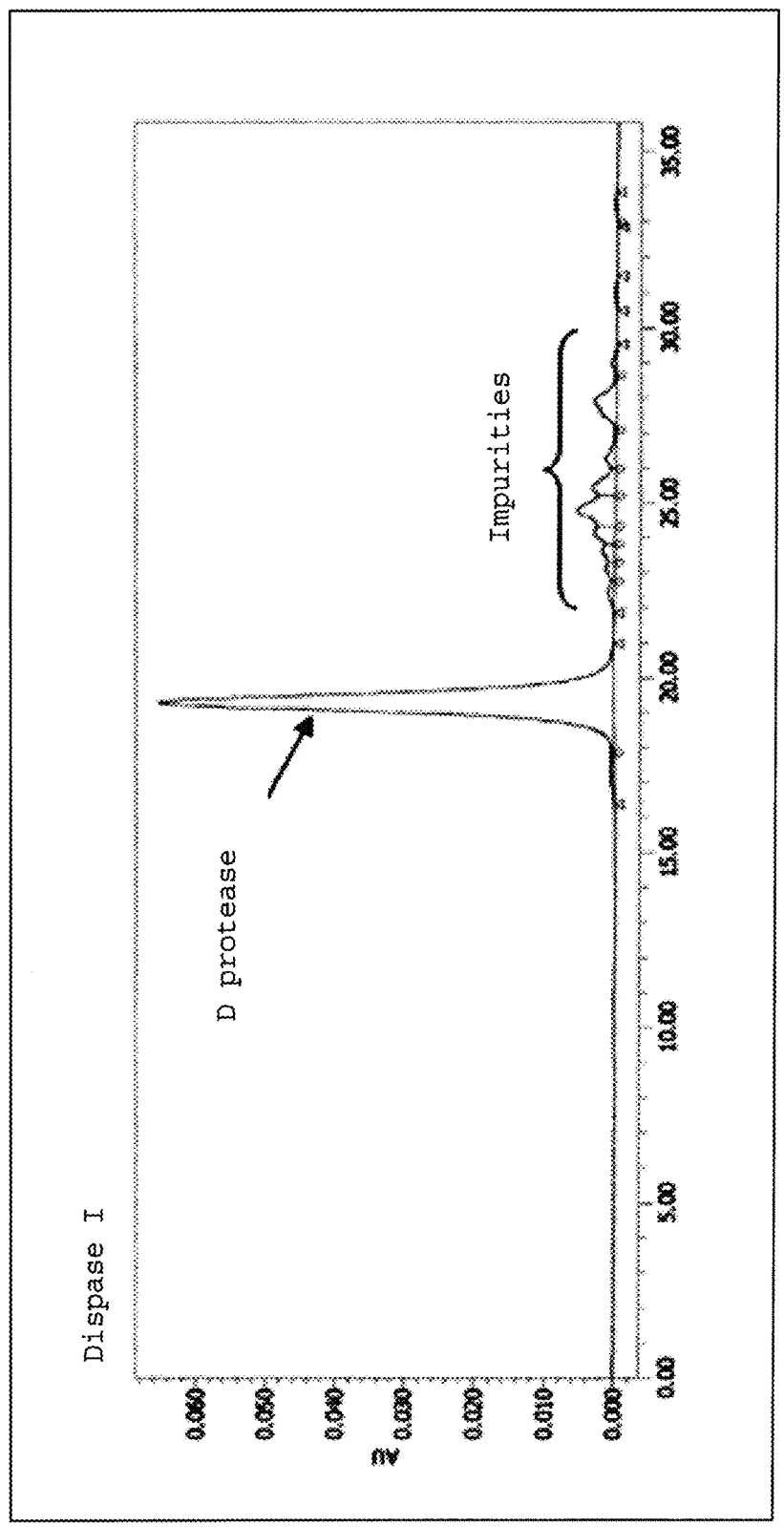
FIG. 2 shows an HPLC gel filtration column chromatogram of Dispase I.
Figure 3:
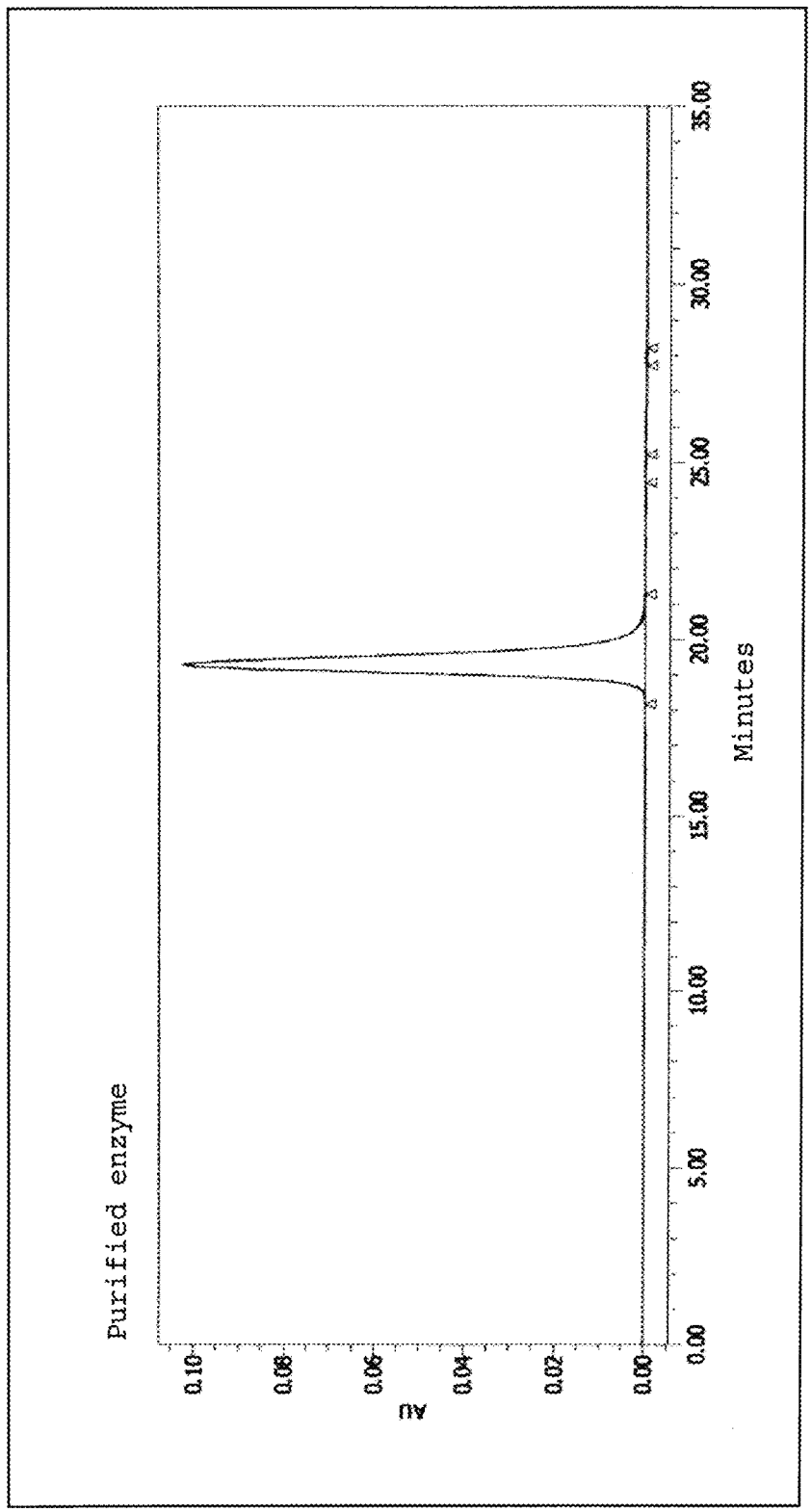
FIG. 3 shows an HPLC gel filtration column chromatogram of a purified enzyme.
Figure 4:
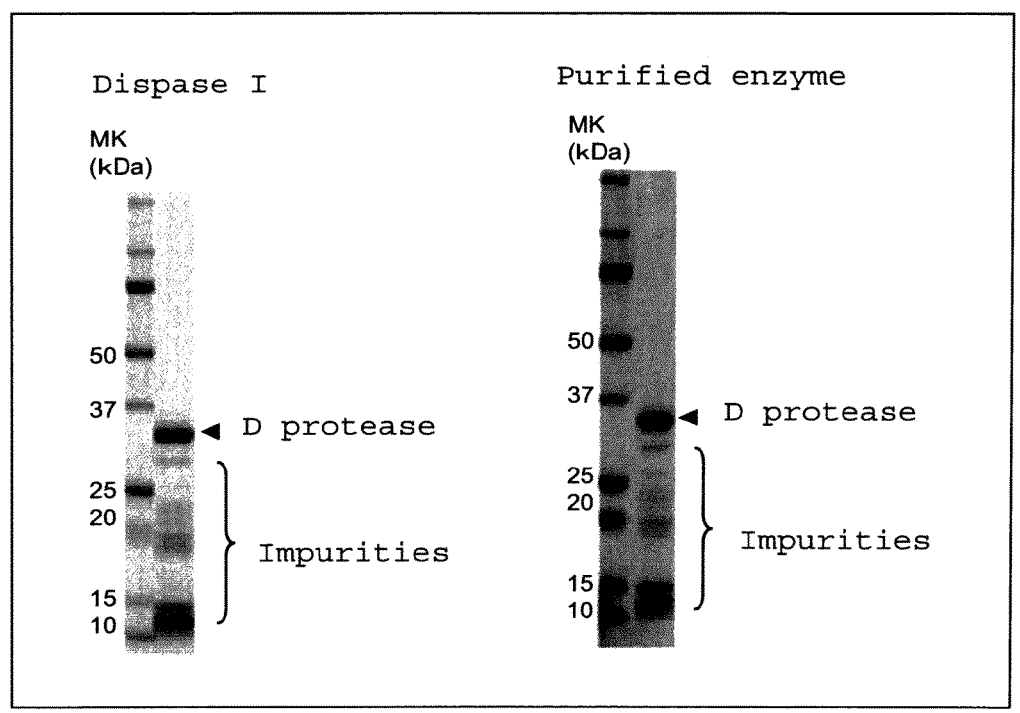
FIG. 4 shows the results of SDS-PAGE of Dispase I and a purified enzyme.

As a result, as shown in FIG. 2 to FIG. 4, a number of bands indicating smaller molecular weights than the band indicating the relevant molecular weight were also detected for the D protease purified by using a DEAE column. This implies that D protease has been degraded in the process of the SDS-PAGE method. Particularly, it was speculated that such degradation was caused by the pretreatment of electrophoresis.

Reference Example 3

Effects of EDTA, Metals and Protein Denaturants

Since D protease is one kind of metalloprotease containing calcium and zinc, it was expected that the degradation of the enzyme during a pretreatment would be suppressed by inactivating the enzyme using a metal chelating agent such as EDTA and a heavy metal other than zinc. Furthermore, it was expected that autologous degradation would be similarly suppressed by instantly denaturing the protein with guanidine, urea, trichloroacetic acid (TCA, pH 4.8) or the like.

Commercially available Dispase I (manufactured by Godo Shusei Co., Ltd.) was dissolved in a 50 mM Tris-2 mM calcium acetate buffer solution (pH 7.5) so that the protein concentration was 2 mg/mL. To 50 µL of this solution, 50 µL each of EDTA, a metal or a protein denaturant at various concentrations was added, and 100 µL of a conventional sample pretreatment liquid (containing 25% glycerin, 2.5% SDS, 0.125 M Tris-hydrochloric acid buffer solution pH 6.8, 2-mercaptoethanol 2.5%, and an appropriate amount of Bromophenol Blue) was added thereto. The resulting mixture was boiled for 3 minutes. Samples that were not boiled as such were also prepared.

The samples thus treated were subjected to SDS-PAGE (15% gel) in an amount of 10 µL each.

Figure 5:
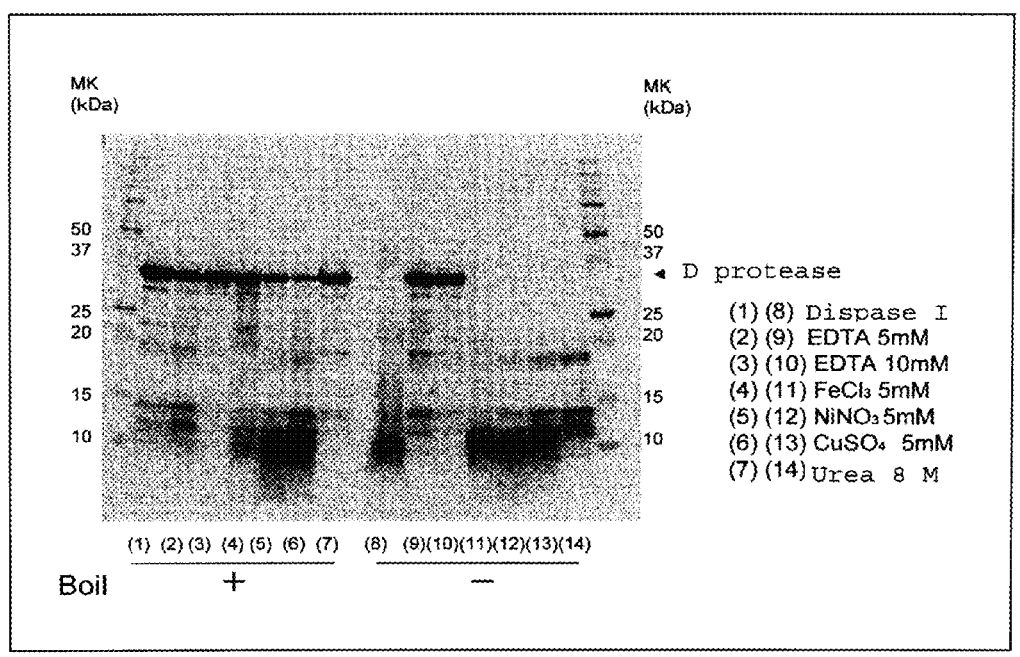
FIG. 5 shows the effects of EDTA, metals and denaturants on SDS-PAGE.

As a result, as shown in FIG. 5, when the mixtures were boiled, EDTA, the metals, the protein denaturants, and the like could not suppress degradation, and the original purity could not be reflected. Impurity bands were detected to the same extent, or to a larger extent, as compared with the case of SDS-PAGE according to a conventional method.

However, in the EDTA 10 mM sample that was not boiled, the band of D protease was darker, and a possibility was speculated that there might be relatively fewer impurity bands.

Reference Example 4

Effects of EDTA

The effects of EDTA were further investigated. Commercially available Dispase I (manufactured by Godo Shusei Co., Ltd.) was dissolved in a 50 mM Tris-2 mM calcium acetate buffer solution (pH 7.5) such that the protein concentration was 2 mg/mL. To 50 µL of this solution, 50 µL each of EDTA at various concentrations was added, and 100 µL of a conventional sample pretreatment liquid (containing 25% glycerin, 2.5% SDS, 0.125 M Tris-hydrochloric acid buffer solution pH 6.8, 2-mercaptoethanol 2.5%, and appropriately amount of Bromophenol Blue) was added thereto (boiling was not carried out). The samples thus treated were subjected to SDS-PAGE (15% gel) in an amount of 10 µL each.

Figure 6:
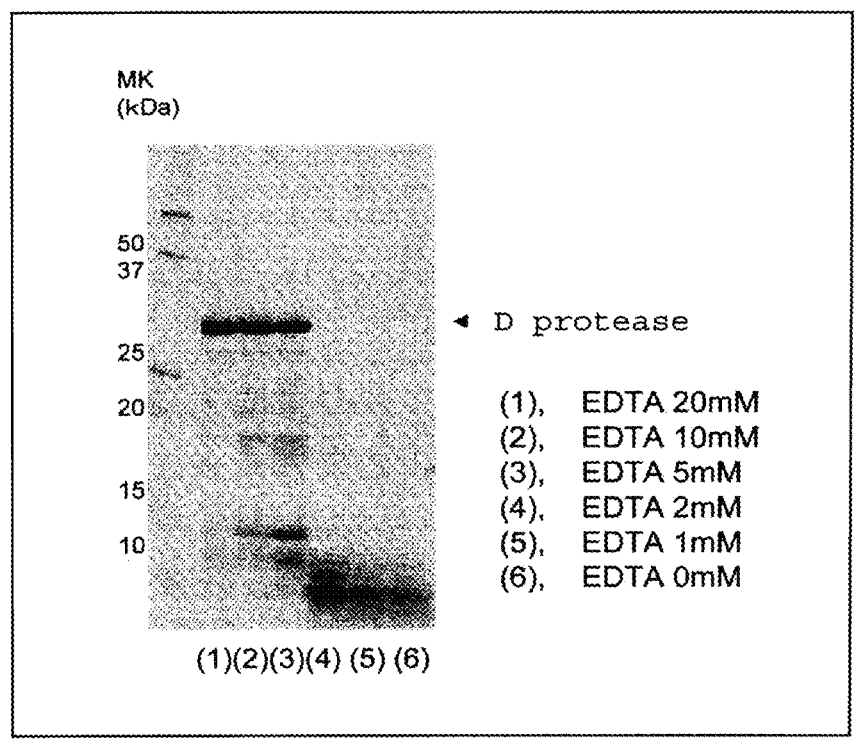
FIG. 6 shows the effects on EDTA and SDS-PAGE.

As a result, as shown in FIG. 6, the number of impurity bands was reduced by 5 mM or higher of EDTA. However, the residual protease activity at the time of separate addition of EDTA was measured, and it was found that the protease activity was maintained as shown in Table 1. Therefore, it was shown that EDTA is not capable of effectively and instantly deactivating the protease activity and reflecting the original purity.

(Method for Measuring Protease Activity)

The measurement of protease activity was carried out using a general casein degradation method. That is, a sample obtained after the addition of EDTA was appropriately diluted with a 50 mM Tris-2 mM calcium acetate buffer solution (pH 7.5), and this dilution was kept warm at 30° C. for 3 minutes in a 1-mL test tube. 5 mL of a 0.6% milk casein solution that had been kept warm at 30° C. in advance was added to the test tube, and the mixture was allowed to react for 10 minutes at 30° C. 5 mL of a precipitating reagent (a reagent prepared by dissolving 18 g of trichloroacetic acid, 18 g of sodium acetate, and 19.8 g of acetic acid in water and adjusting the resultant to 1 mL with water) was added to the reaction mixture, and thereby the reaction was terminated. Precipitates were formed for a while at 30° C., and then the precipitates were filtered using a filter paper. The absorbance of the filtrate at 275 nm was measured. As the blank, a sample that had been inactivated with a precipitating reagent was used.

The results are indicated as relative values calculated by taking the case of a buffer (EDTA-untreated) as 100.

TABLE 1

Activity at the time of sample treatment

| Sample | Activity at the time of inhibitor addition (relative value) |
|---|---|
| EDTA 20 mM | 19 |
| EDTA 10 mM | 38 |
| EDTA 5 mM | 54 |
| Buffer | 100 |

Example 1

Pretreatment with Acid

Since D protease is a neutral protease, it was expected that when the pH at the time of sample treatment is made acidic, the enzyme reaction would be instantly inactivated, and degradation of the enzyme would be suppressed.

Commercially available Dispase I (manufactured by Godo Shusei Co., Ltd.) was dissolved in a 50 mM Tris-2 mM calcium acetate buffer solution (pH 7.5) so that the protein concentration was 2 mg/mL. 50 μL of sulfuric acid at various concentration was added to 50 μL of this solution, and 100 μL of a conventional sample pretreatment liquid (containing 25% glycerin, 2.5% SDS, 0.125 M Tris-hydrochloric acid buffer solution pH 6.8, 2-mercaptoethanol 2.5%, and an appropriate amount of Bromophenol Blue) was added to the mixture. Furthermore, boiled samples were also prepared similarly. The samples thus treated were subjected to SDS-PAGE (15% gel) in an amount of 10 μL each.

Figure 7:
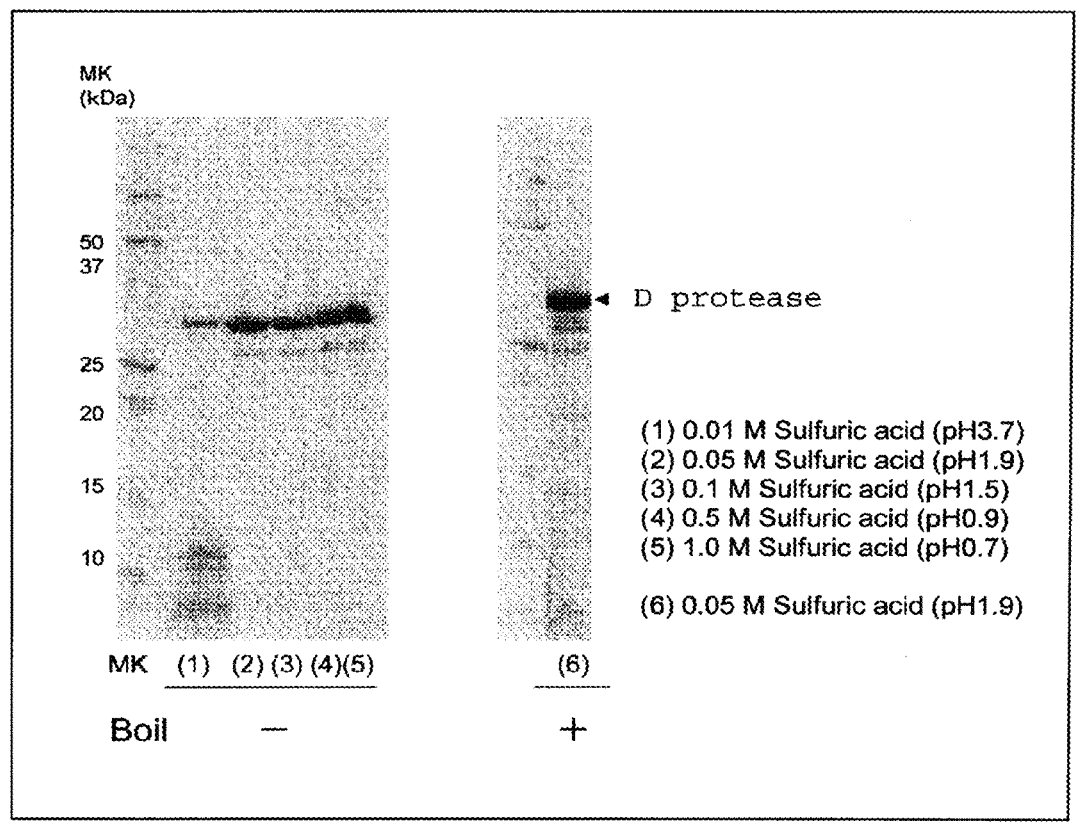
FIG. 7 shows the effects of an acid treatment on SDS-PAGE.

As a result, as shown in FIG. 7, for the 0.05 M sulfuric acid-added samples (pH 1.9), those samples that were boiled showed bands corresponding to degradation products in addition to the D protease band (32 kDa to 34 kDa). On the other hand, for the 0.05 M to 1.0 M sulfuric acid-added samples (pH 0.7 to 1.9), those samples that were not boiled showed a band corresponding to D protease (32 kDa to 34 kDa), and multiple bands were observed, which could be regarded as contaminating proteins having lower molecular weights (less than 32 kDa) than D protease. For the 0.01 M sulfuric acid-added samples (pH 3.7), those samples that were not boiled underwent autodegradation, and therefore, the band corresponding to D protease was thin, while the bands corresponding to degradation products were conspicuously recognized.

That is, it could be seen that when a sample liquid is made acidic by a pretreatment, there are differences in the degradation in accordance with the acidity.

Furthermore, it was found that when SDS is added after the samples are subjected to this acidic condition, SDS-fication proceeds without the boiling operation that is required in the case of adding SDS in a neutral pH range.

Example 2

Effect of Type of Acid

The effect of the type of acid used was checked. Commercially available Dispase I (manufactured by Godo Shusei Co., Ltd.) was dissolved in a 50 mM Tris-2 mM calcium acetate buffer solution (pH 7.5) such that the protein concentration was 2 mg/mL. 50 μL each of various acids was added to 50 μL of the solution, and 100 μL of a conventional sample pretreatment liquid (containing 25% glycerin, 2.5% SDS, 0.125 M Tris-hydrochloric acid buffer solution pH 6.8, 2-mercaptoethanol 2.5% and an appropriate amount of Bromophenol Blue) was added to the mixture.

The samples thus treated were subjected to SDS-PAGE (15% gel) in an amount of 10 μL each.

Figure 8:
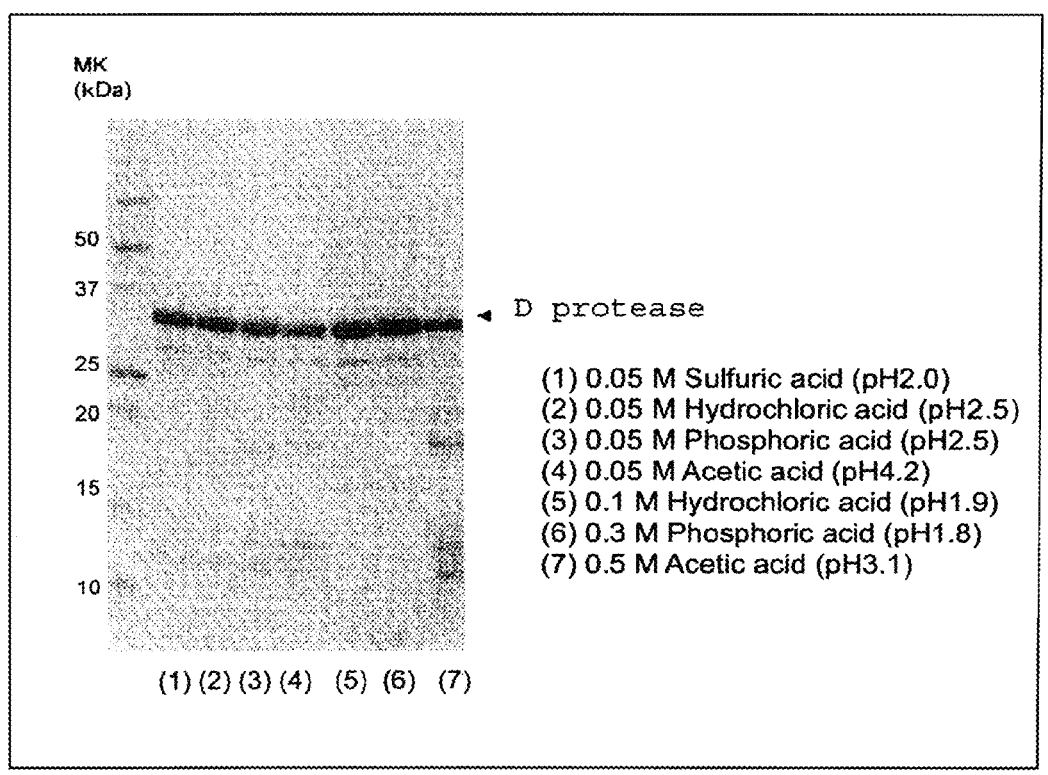
FIG. 8 shows the effects of the type of acid on SDS-PAGE.

As a result, as shown in FIG. 8, the samples exhibited the band corresponding to D protease (32 kDa to 34 kDa) at pH 0.7 to 2.0, irrespective of the type of acid, excluding acetic acid. Further, multiple bands that were considered to correspond to contaminating proteins were observed in a lower molecular weight region than D protease (less than 32 kDa).

Example 3

After an Acid Treatment, the pH is Adjusted to Neutrality and Alkalinity, and then Electrophoresis is Performed Commercially available Dispase I (manufactured by Godo Shusei Co., Ltd.) was dissolved in a 50 mM Tris-2 mM calcium acetate buffer solution (pH 7.5) such that the protein concentration was be 2 mg/mL. 0.5 mL of this sample and an equal amount of 0.05 M sulfuric acid were mixed, and the mixture was subjected to an acid treatment (at this time, pH 1.7). Furthermore, 0.1 M sodium hydroxide was slowly added to this sample while the pH was measured. Thereby, samples in which the pH was returned to neutrality and alkalinity were prepared.

Figure 9:
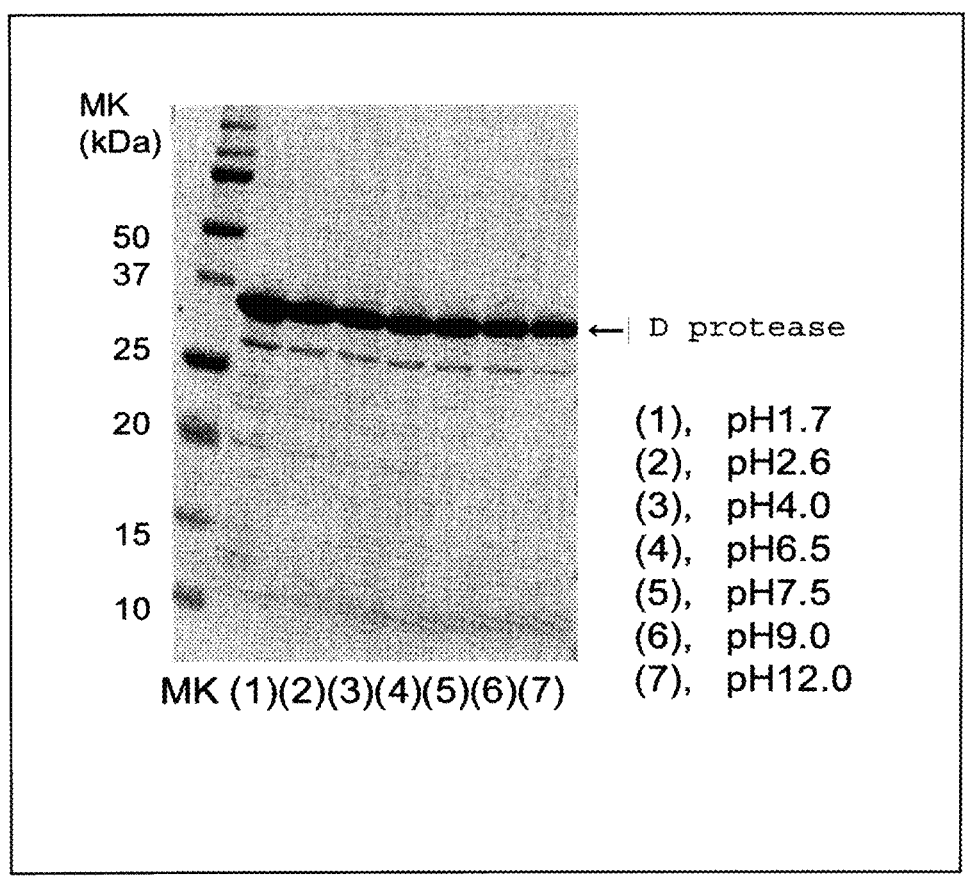
FIG. 9 shows the results of SDS-PAGE when the pH was changed after an acid treatment.

To 50 μL each of samples at various pH values, an equal amount of a sample treatment liquid (containing 25% glycerin, 5% SDS, and an appropriate amount of BPB) was added, and the mixture was thoroughly mixed. Subsequently, 10 μL each of the mixtures was subjected to SDS-PAGE (15% gel). As a result, as shown in FIG. 9, when the pH was changed after the acid treatment, no difference was seen in the electrophoresis results.

Example 4

Alkali Treatment (Near pH 12)

Commercially available Dispase I (manufactured by Godo Shusei Co., Ltd.) was dissolved in distilled water so that the protein concentration was 1 mg/mL. 50 μL of this sample and an equal amount of a sodium hydroxide solution were mixed, and the mixture was subjected to an alkali treatment. The concentration of the sodium hydroxide solution used was changed, and the various pH values were measured.

Figure 10:
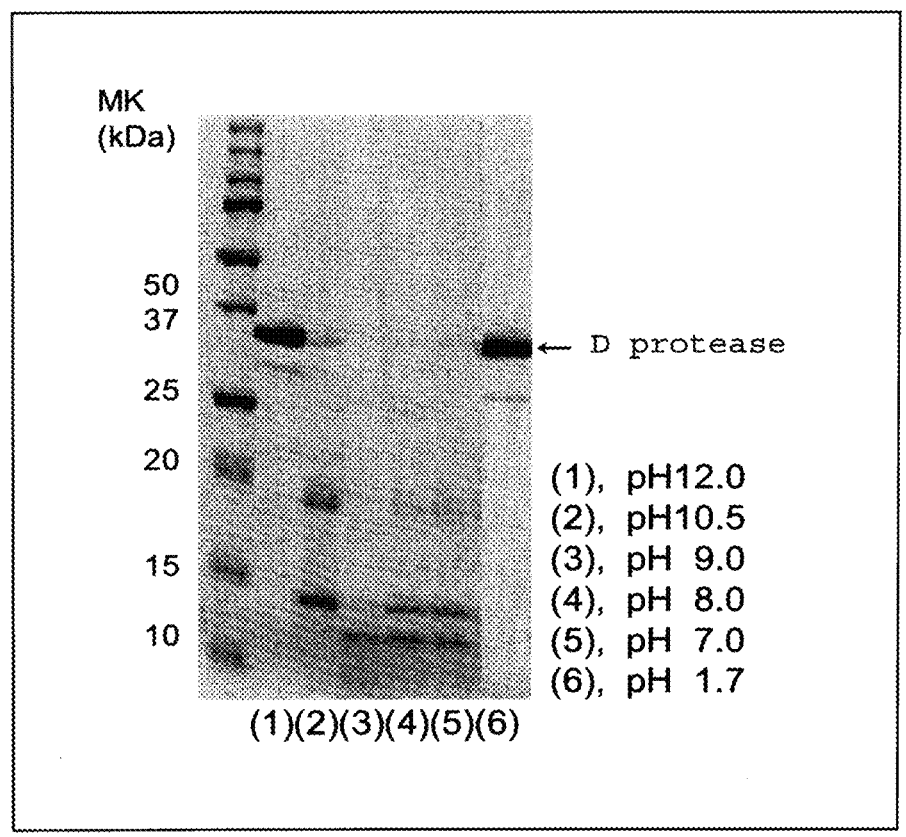
FIG. 10 shows the results of SDS-PAGE after a treatment of a sample with an alkali.

To each of the samples treated with sodium hydroxide solutions at various concentrations, 100 μL of a sample treatment liquid (containing 25% glycerin, 5% SDS, and an appropriate amount of BPB) was added, and the mixture was thoroughly mixed. Subsequently, 10 μL each of the mixtures was subjected to SDS-PAGE (15% gel). As a result, as shown in FIG. 10, even if the samples were subjected to an alkali treatment, the similar electrophoretic patterns as those obtained by an acid treatment method were obtained. However, in the cases of samples which were not brought to a strongly alkaline state at pH 12 or higher, many impurity bands that were considered to correspond to autodegradation products were seen.

Example 5

Comparison of TCA Treatment and Sulfuric Acid Treatment

Commercially available Dispase I (manufactured by Godo Shusei Co., Ltd.) was dissolved in distilled water so as to give a concentration of 5 mg/mL. Furthermore, purified D protease was prepared so as to give a concentration of 50,000 PU/mL (approximately 5 mg/mL). 0.05 mL of this sample and an equal amount of 0.1 M trichloroacetic acid (TCA) or 0.05 M sulfuric acid were respectively mixed to perform an acid treatment. These treatments were all carried out in an ice-cooled state.

To each of the samples thus treated, 0.1 mL of a sample treatment liquid (containing 25% glycerin, 5% SDS and an appropriate amount of BPB) was added, and the mixture was thoroughly mixed. Subsequently, 10 μL each of the samples was subjected to SDS-PAGE (15% gel).

Figure 11:
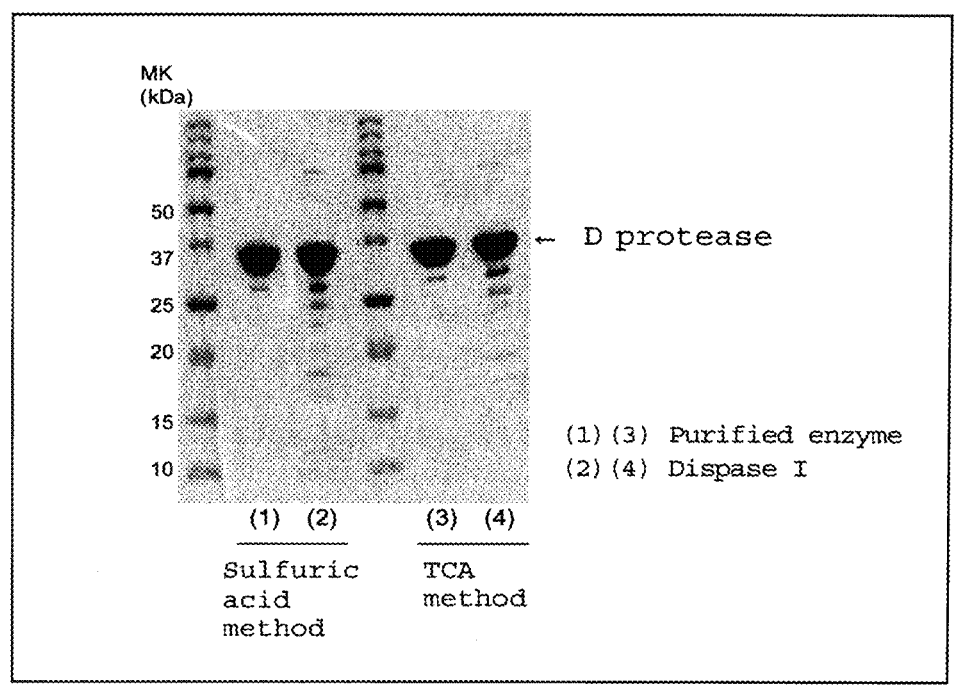
FIG. 11 shows a comparison between a TCA treatment and a sulfuric acid treatment.

As a result, as shown in FIG. 11, the band patterns obtained by a TCA treatment method and a sulfuric acid method were almost the same.

Furthermore, it was shown that the purity of the purified enzyme is about 98%, while the purity of Dispase I is about 90%.

Example 6

Analysis of Purified Enzyme According to Method of Present Invention

The effect of the method of present invention of adding an acid to solutions of commercially available Dispase II (partially purified product), commercially available Dispase I (purified product) and purified enzyme (highly purified product), and then adding a conventional sample treatment liquid, was verified.

Dispase I and II, and the purified enzyme were respectively dissolved in a 50 mM Tris-2 mM calcium acetate buffer solution (pH 7.5) such that the protein concentration was 2 mg/mL. To 50 μL of each sample, 50 μL of 0.05 M sulfuric acid was added, and the mixture was mixed. Subsequently, 100 μL of a conventional sample pretreatment liquid (containing 25% glycerin, 2.5% SDS, 0.125 M Tris-hydrochloric acid buffer solution pH 6.8, 2-mercaptoethanol 2.5%, and an appropriate amount of Bromophenol Blue) was added to the mixture. For a comparison, samples were also prepared by adding and mixing 50 μL of water, instead of 0.05 M sulfuric acid, to each of the enzymes, subsequently adding 100 μL of a conventional sample pretreatment liquid, and boiling the mixture for 3 minutes.

The samples thus treated were each subjected to SDS-PAGE (15% gel) in an amount of 10 μL each.

Figure 12:
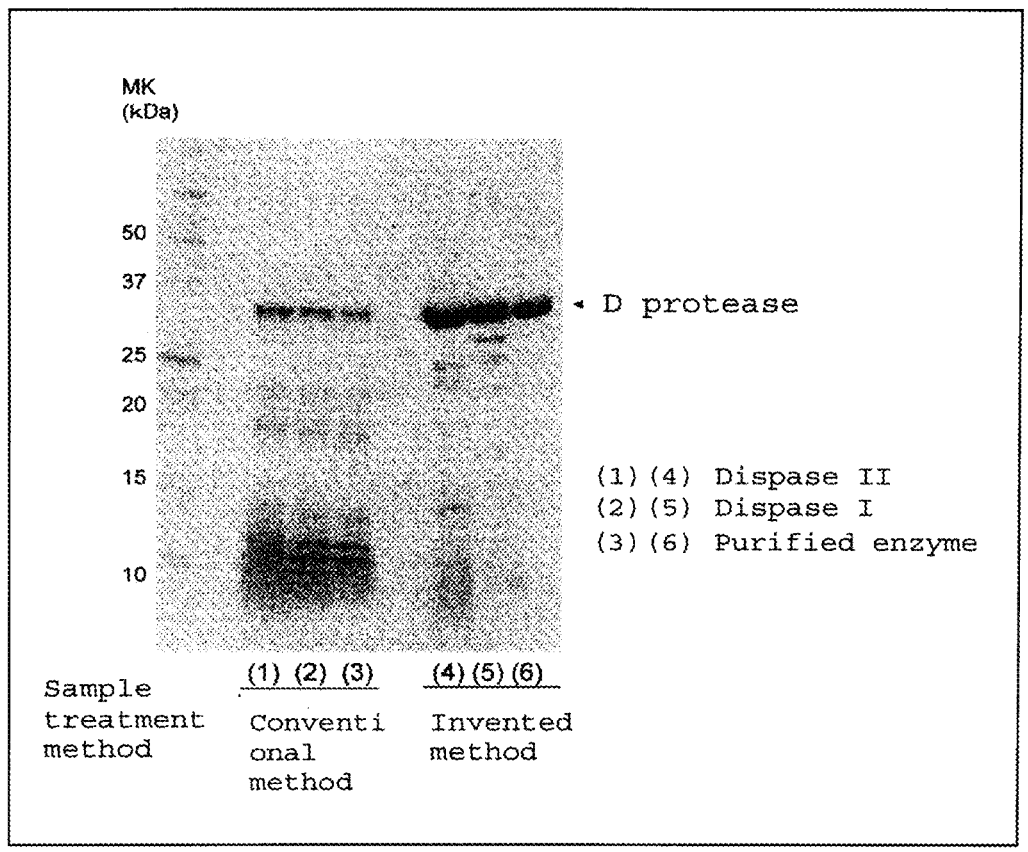
FIG. 12 shows the results of SDS-PAGE of proteases at various purification stages.

As a result, as shown in FIG. 12, when the pretreatment according to the method of the present invention was carried out, D protease and the impurities contained in Dispase I or Dispase II could be clearly observed. Furthermore, it could be observed that the purified enzyme contained decreased impurities. On the other hand, in the conventional method, it could be confirmed that regardless of the degree of purification of the sample, the method does not give results that completely reflect the original purity, and is not suitable for the analysis of the purity of a protease such as D protease.

Example 7

Analysis of Purified Enzyme According to Method of Present Invention: Capillary Electrophoresis Commercially available Dispase I (manufactured by Godo Shusei Co., Ltd.) and the purified enzyme were respectively dissolved in a 50 mM Tris-2 mM calcium acetate buffer solution (pH 7.5) such that the protein concentration was 2 mg/mL.

50 μl of 0.05 M sulfuric acid was added to 50 μL of a sample, and the resulting mixture was mixed. To 4 μL of this mixture, 2 μL of a Bio-Rad sample treatment liquid (Experion Pro260 Analysis Kit, manufactured by Bio-Rad Laboratories, Inc.) and 84 μL of water were added.

For a comparison, 50 μL of water was added to 50 μL of the sample, and the resulting mixture was stirred. Subsequently, to 4 μL of this mixture, 2 μL of a Bio-Rad sample treatment liquid and 84 μL of water were added, and the mixture was boiled. Samples that were not boiled were also similarly prepared.

The samples thus treated were subjected to capillary electrophoresis (Experion fully automated chip electrophoresis apparatus, manufactured by Bio-Rad Laboratories, Inc.).

Figure 13:
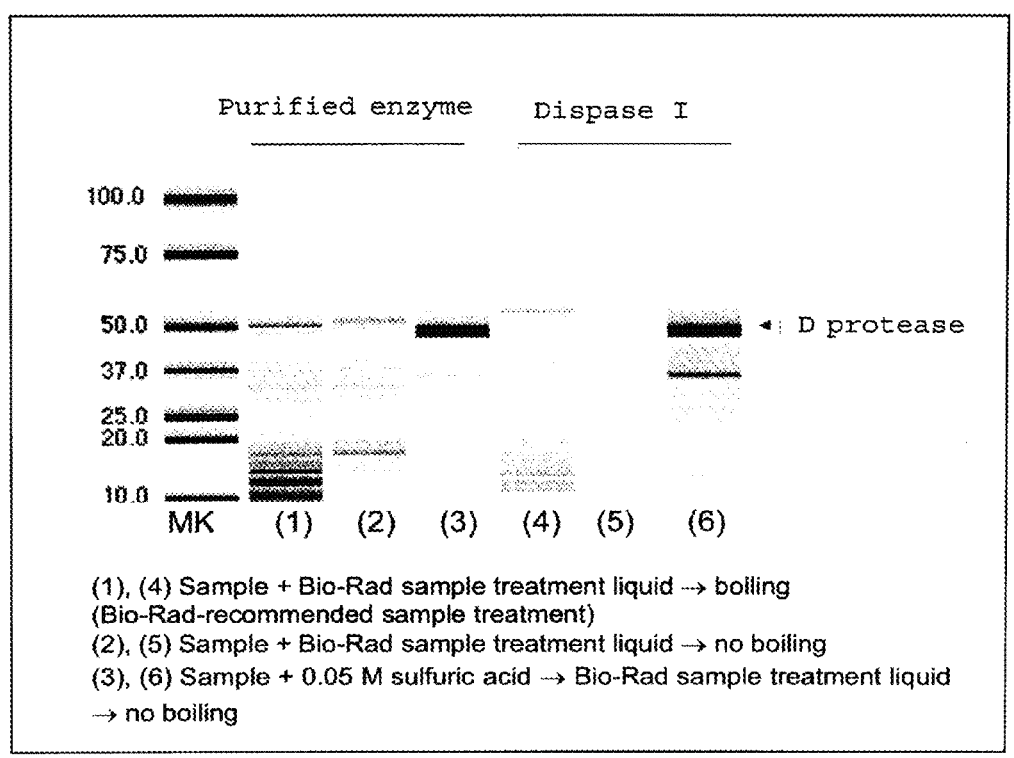
FIG. 13 shows the results of capillary electrophoresis.

As a result, as shown in FIG. 13, when the pretreatment according to the method of the present invention was carried out, a band corresponding to D protease appeared at a molecular weight region of 45 to 50 kDa, and multiple bands that were considered to correspond to contaminating proteins were observed in a lower molecular weight region than the subject enzyme. On the other hand, when the pretreatment according to the present invention was not carried out, a large number of bands corresponding to degradation products were recognized in the molecular weight region of 50 kDa or less.

It was found that the purity of the purified enzyme obtained by this capillary electrophoresis method was 98% or higher, and the purity of Dispase I obtained similarly was 80%.

Example 8

Analysis of Purity of Purified Enzyme

In order to quantify the purity of purified D protease, a calculation according to a serial dilution method was attempted. In order to visualize the impurities band, a series of dilutions prepared from 10 mg/mL of the purified enzyme were subjected to the pretreatment of the present invention, and then were subjected to SDS-PAGE (15% gel). For a comparison, Dispase I was also treated as such. After the process of electrophoresis, it was checked to what extent the impurity bands were included in D protease.

Figure 14:
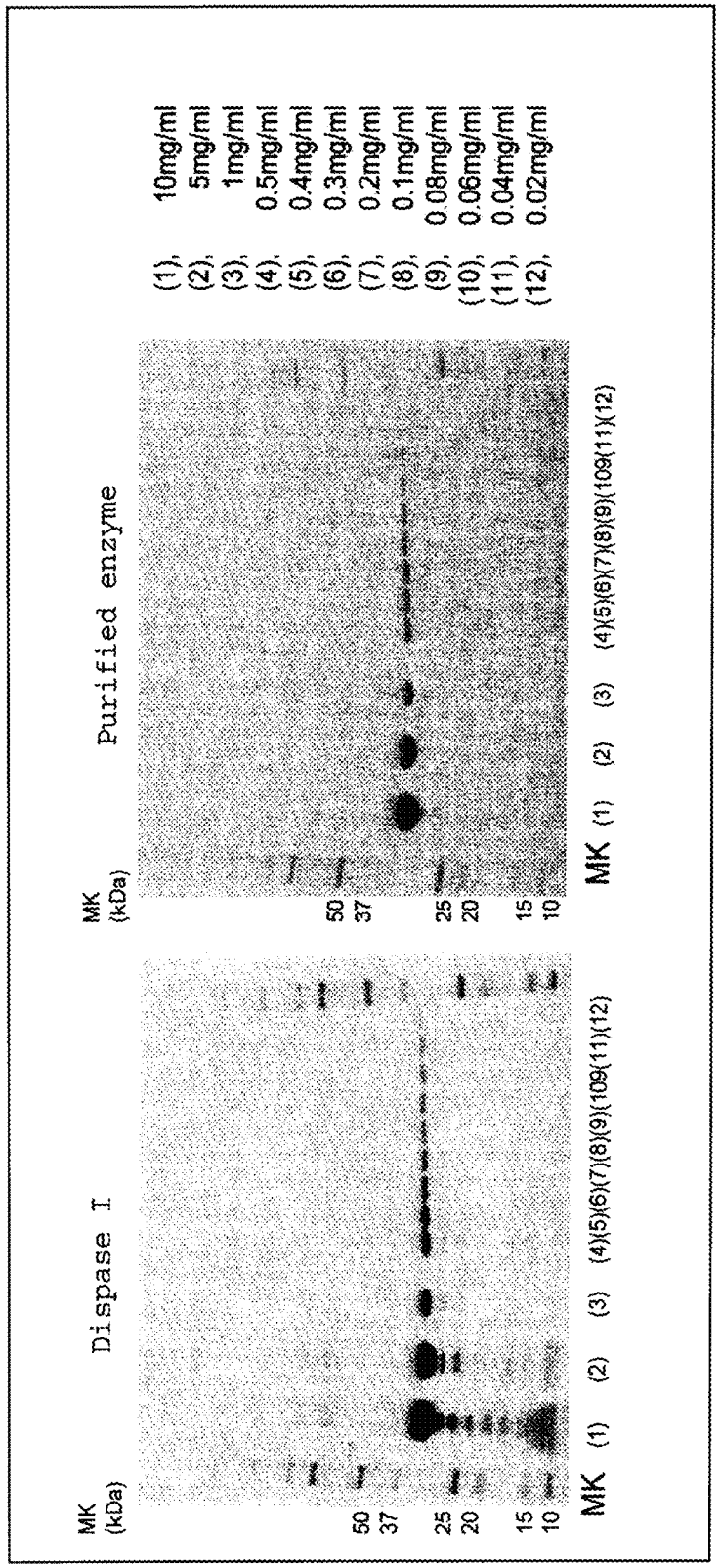
FIG. 14 shows the results of purity inspection by SDS-PAGE (left: Dispase I, right: purified enzyme) after the pretreatment of the present invention.

As a result, it could be seen from FIG. 14 that in the case of the purified enzyme, since the intensity of the band corresponding to 28 kDa to 32 kDa recognized in lane (2) and the intensity of the band corresponding to the subject enzyme in lane (8), which had been diluted to a 1/50 concentration were almost equal, the band corresponding to 28 kDa to 32 kDa in the purified enzyme obtained this time was about 2%.

As such, when Dispase I was analyzed, the total sum of the bands corresponding to less than 32 kDa included about 8 to 12% of a mixture.

Example 9

Analysis of General Protease after Pretreatment According to Present Invention

In order to check whether it is possible to apply the method of the present invention to other proteases, seven kinds of proteases other than D protease were analyzed by the method of the present invention.

Seven kinds of proteases were respectively dissolved in a 50 mM Tris-2 mM calcium acetate buffer solution (pH 7.5) so that the protein concentration was 2 mg/mL. 50 μL of 0.05 M sulfuric acid was added to 50 μL of each of the samples, and the mixture was mixed. Subsequently, 100 μL of a conventional sample pretreatment liquid (containing 25% glycerin, 2.5% SDS, 0.125 M Tris-hydrochloric acid buffer solution pH 6.8, 2-mercaptoethanol 2.5%, and an appropriate amount of Bromophenol Blue) was added to the mixture.

For a comparison, samples were also produced by adding and mixing 50 μL of water instead of 0.05 M sulfuric acid, subsequently adding 100 μl of a sample treatment liquid that is used in conventional methods, and boiling the mixture for 3 minutes.

The samples thus treated were subjected to SDS-PAGE (15% gel) in an amount of 10 μL each.

Figure 15:
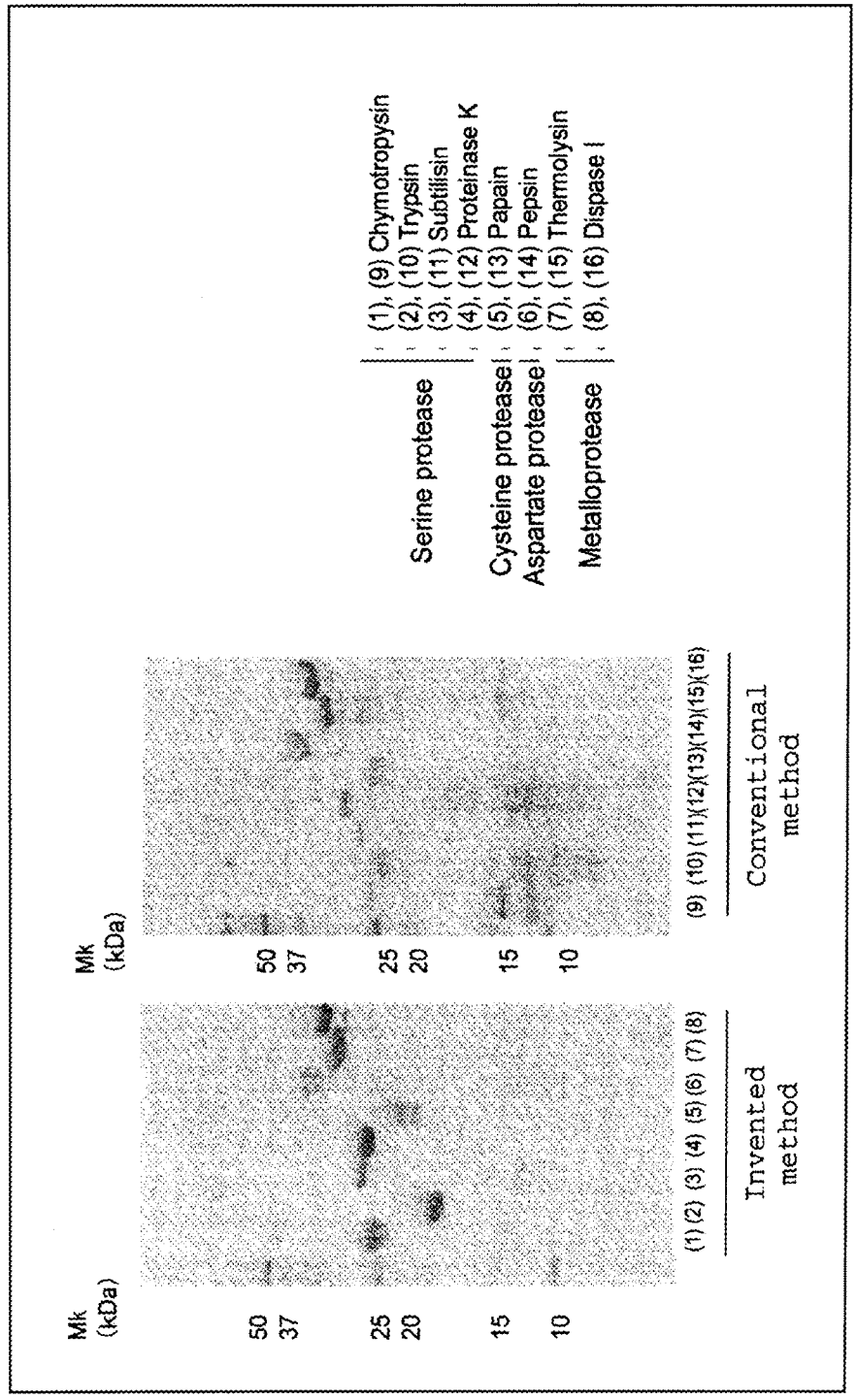
FIG. 15 shows the results of an analysis (comparison of pretreatment methods) of various proteases.

As a result, as shown in FIG. 15, as the pretreatment of the present invention using an acid was carried out, the bands on SDS-PAGE corresponding to the proteases were dark, irrespective of the kind of proteases (difference in the active center), except for pepsin which is an acidic protease, and the number and amounts of other bands included in those lanes were decreased. This implies that the occurrence of autodegradation of proteases in the conventional pretreatments or the degradation of co-existing proteins is suppressed by the pretreatment method of the present invention.

Example 10

Verification of Properties of D Protease

The optimum pH, pH stability and optimum temperature of D protease were measured. Further, the molecular weight was estimated from the results of SDS-PAGE.

i) Optimum pH (Patent Document 1: pH 8.5)

Commercially available Dispase I was diluted to 50 PU/mL with buffers respectively adjusted to various pH values. Substrates were provided by preparing 0.6% milk casein with buffers respectively adjusted to various pH values, and the protease degradation activity was measured at various pH values. The substrate and the enzyme were mixed separately for cases, and the pH at the time of reaction was measured.

Meanwhile, a 50 mM Mes-2 mM calcium acetate buffer was used for pH 5.5 and 6.5; a 50 mM Tris-2 mM calcium acetate buffer was used for pH 7.5 and 8.5; and a 50 mM Chaps-2 mM calcium acetate buffer was used for pH 9.5, 10.5 and 11.0.

Figure 16:
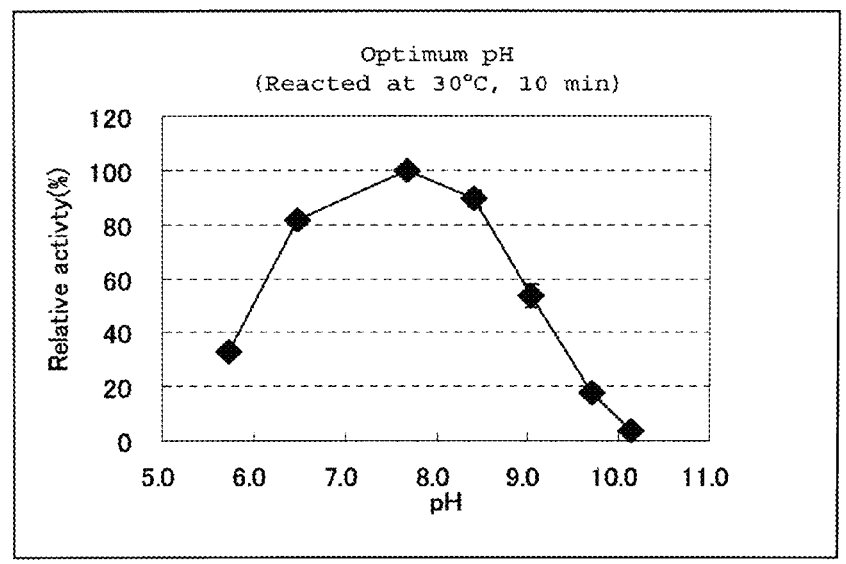
FIG. 16 shows the optimum pH of D-protease.

As a result, the optimum pH of D protease was 7.0 to 8.0 (FIG. 16).

ii) pH Stability (Patent Document 1: pH 4 to 9)

Commercially available Dispase I was diluted to 6500 PU/mL with buffers that had been adjusted to various pH values, and the dilutions were stored for one hour at various temperatures such as 4° C., 37° C., 45° C., 50° C., 55° C. and 60° C. Each of the samples was diluted to 50 PU/mL with a 50 mM Tris-2 mM calcium acetate buffer (pH 7.5), and the protease activity (pH 7.5) was measured.

Meanwhile, a 50 mM Mes-2 mM calcium acetate buffer was used for pH 5.5 and 6.5; a 50 mM Tris-2 mM calcium acetate buffer was used for pH 7.5 and 8.5; and a 50 mM Chaps-2 mM calcium acetate buffer was used for pH 9.5, 10.5 and 11.0.

Figure 17:
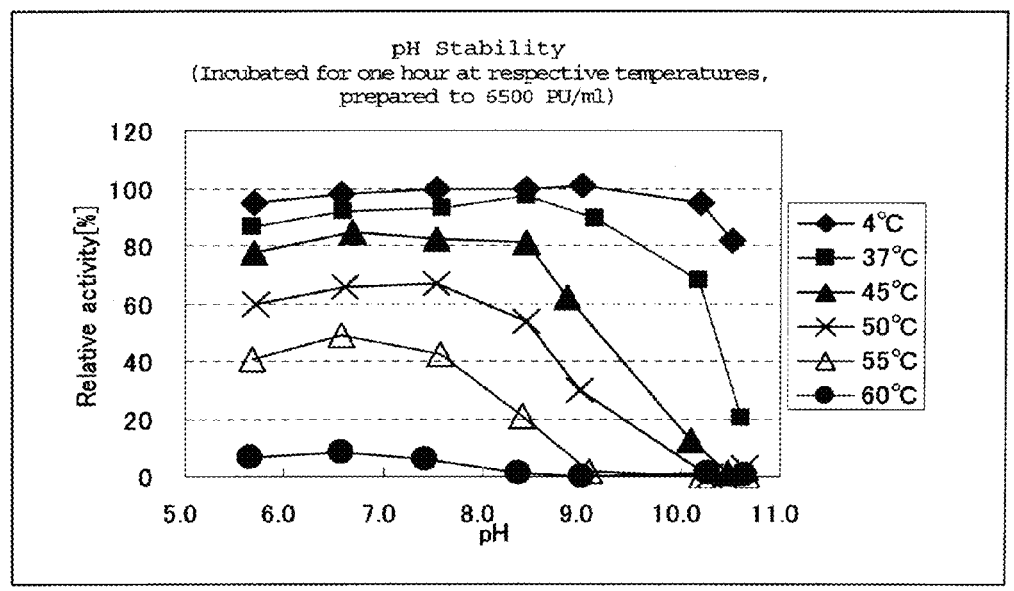
FIG. 17 shows the pH stability of D-protease.

As a result, D protease was stable at pH 5.5 to 9.0 (FIG. 17).

iii) Optimum Temperature (Patent Document 1: 60° C.)

Commercially available Dispase I was diluted to 50 PU/mL with a 50 mM Tris-2 mM calcium acetate buffer (pH 7.5), and the protease activity (pH 7.5) was measured at various temperatures such as 30° C., 40° C., 50° C., 55° C. and 60° C.

Figure 18:
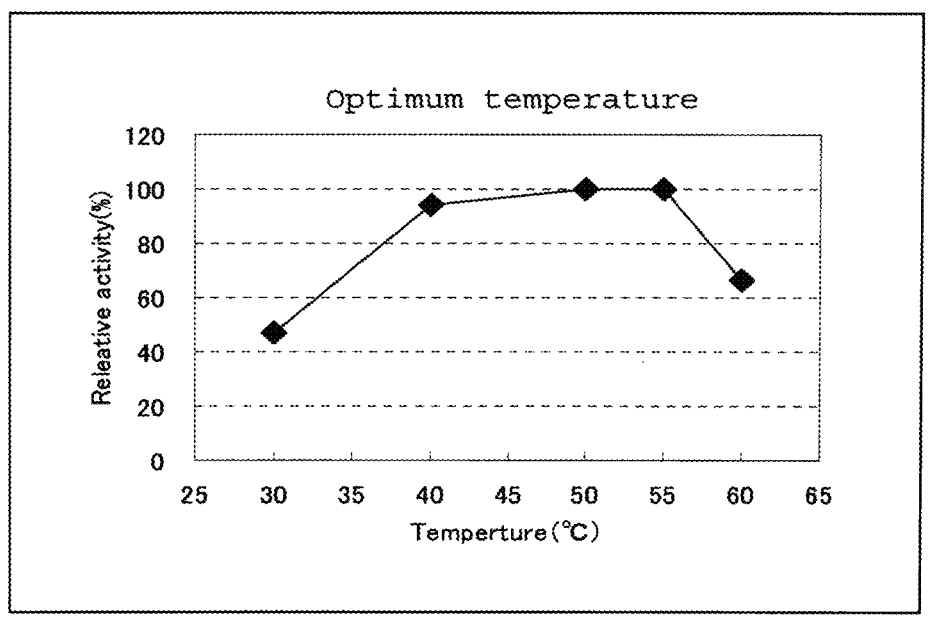
FIG. 18 shows the optimum temperature of D-protease.

As a result, the optimum temperature of D protease was 55° C. (FIG. 18).

iv) Measurement of Molecular Weight (Patent Document 1: 35,900 Da According to Ultracentrifugation Method)

Commercially available Dispase I was dissolved in a 50 mM Tris-2 mM calcium acetate buffer solution (pH 7.5) such that the protein concentration was 2 mg/mL. 50 μL of 0.05 M sulfuric acid was added to 50 μL of the sample, and the mixture was mixed. An equal amount of a sample treatment liquid (containing 25% glycerin, 5% SDS and an appropriate amount of BPB) was added to the mixture, and the resultant was thoroughly mixed. Subsequently, the samples were subjected to SDS-PAGE (15% gel).

Figure 19:
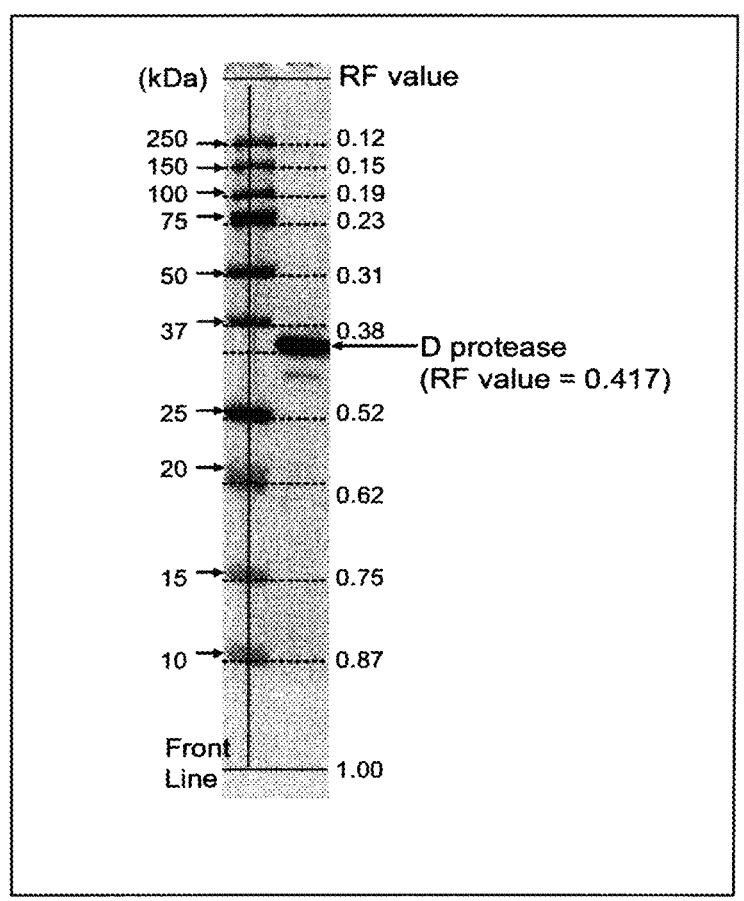
FIG. 19 shows the results of SDS-PAGE of D-protease.

After the process of electrophoresis, the molecular weight of D protease was estimated from the mobility (RF value) of the band corresponding to D protease and the band corresponding to the marker protein molecule, and as a result, the molecular weight was found to be 32 to 34 kDa (FIG. 19).

The invention claimed is:

1. An electrophoretic analysis method for analyzing a protease-containing sample, comprising:
   exposing a sample comprising a protease to be analyzed to a pH condition under which the protease is deactivated within one minute, and then
   subjecting the sample to electrophoresis.

2. The analysis method of claim 1, wherein the pH condition under which the protease is deactivated different from an optimum pH of the protease by a value of 3 or greater.

3. The analysis method of claim 1, wherein:
   the protease is a neutral protease, and the pH condition under which the protease is deactivated is pH 0.1 to 3 or pH 11 to 14;
   the protease is an acidic protease, and the pH condition under which the protease is deactivated is pH 10 to 14; or
   the protease is an alkaline protease, and the pH condition under which the protease is deactivated is pH 0.1 to 4.

4. The analysis method of claim 1, wherein the protease is a neutral metalloprotease, and the pH condition under which the protease is deactivated is pH 0.7 to 2.0 or pH 12 to 14.

5. The analysis method of claim 1, which analyzes a purity of a protease.

6. The analysis method of claim 1, wherein the electrophoresis is SDS-PAGE or capillary electrophoresis.

7. The analysis method of claim 1, wherein the protease (1) is produced by a bacterium of genus *Paenibacillus*; (2)

degrades casein and hemoglobin in a neutral pH range; (3) has an optimum pH of 7.0 to 8.0, and is stable at pH 5.5 to 9.0; (4) works at 20° C. to 75° C., and has an optimum temperature of 55° C.; and (5) has a molecular weight estimated to be 32,000 to 34,000 Da according to an electrophoresis method, and the pH condition under which the protease is deactivated is pH 0.7 to 2.0 or pH 12 to 14.

8. A protease, having a purity of 92% or higher as measured by the analysis method of claim 1, wherein the protease
   (1) is produced by a bacterium of genus *Paenibacillus*;
   (2) degrades casein and hemoglobin in a neutral pH range;
   (3) has an optimum pH of 7.0 to 8.0, and is stable at pH 5.5 to 9.0;
   (4) works at 20° C. to 75° C., and has an optimum temperature of 55° C.; and
   (5) has a molecular weight estimated to be 32,000 to 34,000 Da according to an electrophoresis method.

9. The protease of claim 8, having a purity of 95% or higher.

10. The analysis method of claim 1, wherein the protease is deactivated within 10 seconds.

11. The analysis method of claim 1, wherein the pH condition under which the protease is deactivated is different from an optimum pH of the protease by a value of 4 or greater.

12. The analysis method of claim 1, wherein the protease is D protease.

13. The analysis method of claim 12, wherein the electrophoresis is SDS-PAGE with an SDS treatment performed at 10° C. to 30° C.

14. The analysis method of claim 1, wherein the protease is D protease, and the pH condition under which the protease is deactivated is 0.7 to 2.0.

15. The analysis method of claim 1, wherein the protease is D protease, and the pH condition under which the protease is deactivated is 0.9 to 1.9.

16. The analysis method of claim 1, wherein the protease is D protease, and the pH condition under which the protease is deactivated is 1.5 to 1.9.

17. The analysis method of claim 1, wherein the exposing is performed at 25° C. for 1 to 30 minutes.

18. The analysis method of claim 1, wherein the exposing is performed at 25° C. for 1 to 10 minutes.

19. The protease of claim 8, having a purity of 98% or higher.

20. The protease of claim 8, having a purity of 99% or higher.

* * * * *